US008357902B2

(12) United States Patent
Chawla (10) Patent No.: US 8,357,902 B2
(45) Date of Patent: Jan. 22, 2013

(54) APPARATUS FOR DETECTING AND IMAGING EXPLOSIVES ON A SUICIDE BOMBER

(75) Inventor: Manmohan S. Chawla, University Park, MD (US)

(73) Assignee: System Planning Corporation, Arlington, VA (US)

( * ) Notice: Subject to any disclaimer, the term of this patent is extended or adjusted under 35 U.S.C. 154(b) by 0 days.

(21) Appl. No.: 13/236,990

(22) Filed: Sep. 20, 2011

(65) Prior Publication Data

US 2012/0175521 A1 Jul. 12, 2012

Related U.S. Application Data

(60) Provisional application No. 61/386,398, filed on Sep. 24, 2010.

(51) Int. Cl.
G01J 5/10 (2006.01)
G01J 3/28 (2006.01)

(52) U.S. Cl. ........... 250/341.1; 250/339.02; 250/339.11; 250/341.8

(58) Field of Classification Search ............... 250/339.02
See application file for complete search history.

(56) References Cited

U.S. PATENT DOCUMENTS

| 6,909,104 | B1 | 6/2005 | Koops |
| 2004/0041724 | A1 | 3/2004 | Levitan et al. |
| 2004/0065831 | A1 | 4/2004 | Federici et al. |
| 2004/0183712 | A1 | 9/2004 | Levitan et al. |
| 2005/0230604 | A1 | 10/2005 | Rowe et al. |
| 2005/0232459 | A1 | 10/2005 | Rowe et al. |
| 2006/0054824 | A1 | 3/2006 | Federici et al. |
| 2007/0235658 | A1* | 10/2007 | Zimdars et al. .......... 250/390.07 |
| 2009/0045343 | A1* | 2/2009 | Breit et al. ................. 250/341.8 |
| 2010/0278441 | A1* | 11/2010 | Shashidhar .................. 382/218 |

FOREIGN PATENT DOCUMENTS

GB    2411093 A1    8/2005

OTHER PUBLICATIONS

Pica, Albert, "Explosive Personnel Screening Via Terahertz Spectroscopy", Sarnoff Corporation.
Zandonella, Catherine, "T-ray Spectroscopy", Nature, Aug. 2003, vol. 24, pp. 721-722.
Mittleman, Daniel et al., "T-ray Imaging", IEEEJ of Selected Topics in Quantum Electronics, Sep. 1996, vol. 2, No. 3.
Langlin Wang et al., "Metal Wires for Terahertz Waveguiding", Nature, Nov. 18, 2004, vol. 432.
Mueller, Eric R., "Terahertz Radiation Apparatus and Sources", Industrial Physicists, Aug./Sep. 2003.
Clery, Daniel, "Brainstorming Their Way to an Imaging Revolution", Science, Aug. 2002, vol. 297, pp. 761-762.
Woodward, Ruth M., "Terahertz Technology in Medicine and Pharmaceutical Industry", Preclinica, Sep./Oct. 2004, vol. 2, No. 5.
Wang, S. et al., "Pulsed Terahertz Tomography", J. Appl Phy D, Applied Physics 37, 2004, R1-R36.

(Continued)

*Primary Examiner* — Marcus Taningco (57) ABSTRACT

An apparatus designed for generating and detecting reflected Terahertz waves using a single pixel Complementary Metal Oxide Semiconductor (CMOS) or Charge Couple Device (CCD) camera is described. Optical alignment between the components is not necessary since the Terahertz waves can propagate from the source to a collimating lens using a metal wire that can be bent obviating the need to have a clear line of sight from the lens to the source or to the camera. The present invention is well-suited for high traffic physical locations currently under surveillance such as security check points and also venues demanding significantly less obtrusive surveillance such as revolving entry doors, moving walkways, and entry gates for airplanes.

5 Claims, 5 Drawing Sheets

OTHER PUBLICATIONS

Wang, S., "Terahertz Imaging and Tomography", J. Bio Phy 29, 2003, pp. 247-256.

Savage, Neil, "T-ray Advance Toward Airport Screening", MIT Technology Review, Feb. 20, 2007.

Lui H.C., "Terahertz Semiconductor Quantum Well Devices", Chinese Journal of Semiconductor, Apr. 2006, vol. 27, No. 4, pp. 627-634.

* cited by examiner

APPARATUS FOR DETECTING AND IMAGING EXPLOSIVES ON A SUICIDE BOMBER

BACKGROUND OF THE INVENTION:

1. Field of the Invention

The present invention relates to a device and method for detecting explosives. More particularly, the present invention relates to an apparatus and method for generating and detecting Terahertz radiation to positively identify explosive devices carried on human or animal subjects.

2. Description of Related Art

Recent advancements in generation and detection techniques have opened up new opportunities in explosive imaging. More specifically, significant advancements have been made in the use of Terahertz radiation. With current advances, low-power, Terahertz frequencies can be efficiently generated to irradiate a human subject positioned at a short distance from the source.

It is known that organic molecules have unique vibrational and rotational frequencies and that the rotational frequencies lie in the Terahertz regime. The Terahertz waves also have the capability to excite these rotational frequencies within the molecules of explosive materials. The commonly used explosive RDX, for example, has spectral lines at 0.82, 1.05, 1.50, 1.96, 2.20, 3.08 and 6.73 THz. A simultaneous detection of these rotational frequencies or wavelengths through several layers of clothing will constitute a very robust detection of RDX. Other explosives can be similarly detected. In addition to spectral specificity, good imaging resolution is inherently possible as the wavelengths associated with Terahertz waves are short. However, privacy concerns still exist in this kind of imaging.

The role Terahertz frequencies can play in the detection of explosives has been known for some time. However, it has been difficult to make robust THz sources or detectors. Terahertz frequencies (0.5 to 5.0 THz) occupy the region of electromagnetic spectrum that is sandwiched between microwaves and infrared. These frequencies are too high to be produced by conventional electronics and too low to be produced by solid state lasers. Accordingly, the conventional sources of THz are ultra-fast laser switches, pumped gas lasers, optical difference generation techniques, frequency doubling diodes and quantum cascade lasers. All of these require cumbersome equipment and large power sources.

Other detection systems like the Ion Mobility Spectrometer require a small sample of the explosive to be physically brought to the machine for analysis. In the end, none of the prior art discloses an effective and efficient way to detect explosives. Therefore, a need exists to develop a novel alternative that can detect and positively identify explosives in real time without the drawbacks evident in the prior art.

SUMMARY OF THE INVENTION

The object of the present invention is to overcome the shortcomings disclosed in the prior art. The technique of the present invention is based on illuminating human subjects, one at a time or in groups, by very low power Terahertz waves and then looking for the spectral signatures or the fingerprints of explosives in the reflected energy. Most explosives selectively absorb are Terahertz frequencies. Accordingly, the reflected spectrum will show features corresponding to the lines that were absorbed and will thus allow positive identification of an irradiated target.

According to one aspect of the present invention, detecting explosives through clothing may be facilitated by a miniaturized, inexpensive, low-power Terahertz device radiating continuously as described in U.S. Pat. No. 6,909,104 to Koops et al. This device consists of a semiconductor chip on which a source of electrons, an arrangement of electrostatic lenses, an accelerating grid, an anode and a grating are provided along with focusing electronics.

According to a further aspect of the present invention, detecting explosives through clothing may be facilitated by designing a plurality of miniature Terahertz sources and CMOS or CCD imaging cameras to be incorporated in the revolving entry doors of airports, along moving walkways, at security check points and the like. Accordingly, a human subject may be unobtrusively examined for potential explosive devices without sensing entry or exit through examination processing points.

The accompanying drawings, which are incorporated in and constitute part of the specification, illustrate various embodiments of the invention and together with the description, serve to explain the principles of the invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended and such alterations and further modifications in the illustrated devices are contemplated as would normally occur to one skilled in the art.

Figure 1:
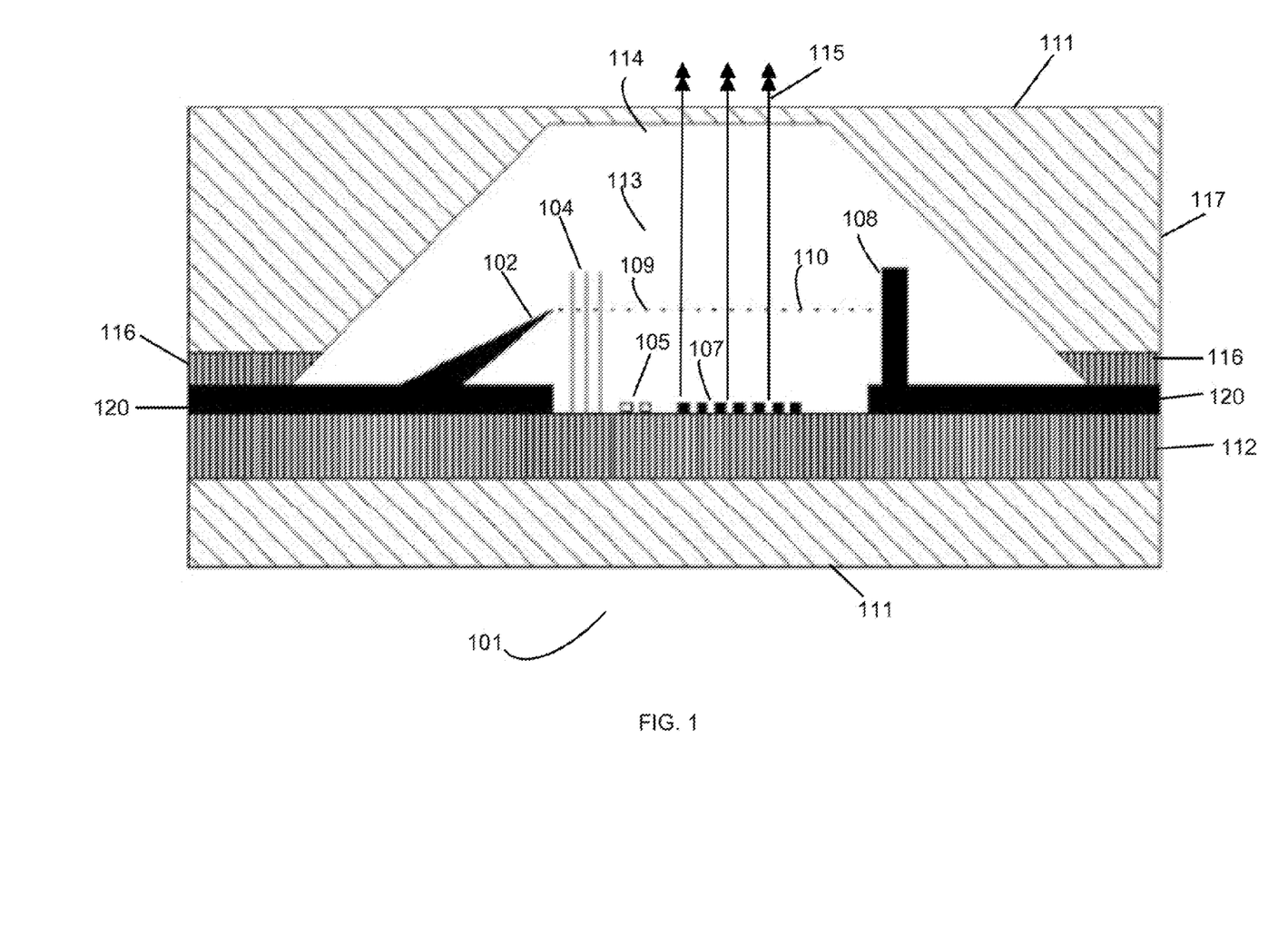
FIG. 1 shows an example of a Terahertz semiconductor chip as known in prior art.

According to the present invention, a miniaturized Terahertz radiation source is provided to generate THz frequencies. A miniaturized Terahertz source based on the Smith-Purcell effect, may be integrated on a semiconductor chip which may emit continuous polarized radiation at the microwatt level in accordance with U.S. Pat. No. 6,909,104 B1 except that the periodicity of the grating is variable to produce a broadband source in the frequency regime ranging from 0.3 to 0.4 Terahertz. The detailed operation of an exemplary chip is further detailed in U.S. Pat. No. 6,909,104 B1 to Koops et al., which is hereby incorporated by reference. As shown in FIG. 1, an exemplary miniaturized Terahertz radiation source 101 according to one of the aspects of the present invention is provided.

As shown, the radiation source 101 is comprised of field emitters 102 linked via electrical terminals 120, an electrostatic lens 104 comprised of three electrodes for focusing electron beams 109/110, a beam deflector 105 for deflecting the beams in a horizontal and/or vertical direction, and a grating 107 of metal having an integrated reflector. According to one aspect of the present invention, the grating 107 preferably incorporates additive nanolithography on an insulating substrate having a Terahertz reflection base in the grating region and/or on metal conductor connection structures. Preferably, the structures are prefabricated using an electron beam or optical lithography, and encapsulated in a vacuum 113 using a technology which is transparent to Terahertz radiation. This design enables the electron beam 109 emerging from the field emitter 102 to be focused through the miniaturized wire lenses 104, and to be directed through integrated deflecting plates 105, thereby generating Terahertz radiation whose intensity and wavelength may be varied and selected.

Preferably, the radiation from the electron source may be retained at a constant level by a control circuit, and more particularly, by a controllable voltage source. As further shown in FIG. 1, the electron beam 110 propagating over the grating 107 may then be picked up by a second anode 108, which may be used as a collecting anode. Between the second electrode of the electrostatic lens 104 and second anode 108, a field may be applied, which may be used to alter the electron velocity along the grating. This may be used for precisely adjusting the wavelength and also for generating a frequency spectrum.

As further shown in FIG. 1, by providing encapsulation using a silicon membrane 112, the emitted laser THz radiation 115 is radiated to the outside through a membrane window 114. The radiation emitter, constructed on a chip of silicon 111 and composed of the field emission source, optics, grating and anode, may be covered in this exemplary embodiment by a membrane window 114, which may preferably be made of silicon 111, as may be the entire covering chip 117. A membrane window 114 covering a chip 117 may be treated using reflection-reducing layers, so that a maximum transmission through the window 114 may be attained for the frequency range of the emitted radiation.

Further, configured underneath the grating region may be a THz radiation reflector in the form of a metal layer or arrangement of grating rods, having a defined spacing of a suitable period. The grating may be made of magnetic or non-magnetic materials, so THz radiation 115, which exits grating 107 in the direction of the substrate, may be sent back through the grating with the highest possible reflectance, thereby strengthening the intensity of the emitted radiation. Implementing a beam guidance over the grating 107 at a defined distance may allow variations of the intensity of the radiation source. This means that by employing a deflecting element 105 before the grating, the radiated intensity may be modulated in response to the application of an alternating current voltage pass the deflecting element.

In accordance with a preferred embodiment of the present invention, the free electron beam passing just above the metallic grating is modulated by the periodicity of the lines on the grating which ranges from 0.1 mm to 0.1 µm. The height above the grating, the velocity of electrons and the grating constant determine the wavelength of the radiation. Preferably, according to one aspect of the invention, the radiation is coherent and polarized. Further, preferably, the power level is kept small at the 1 µw level.

For generating Terahertz waves of constant frequency and to detect specific explosives, the grating constant may be fine-tuned to the explosive's absorption band. However, for detecting a variety of explosives, a broadband of frequencies ranging from 0.1 to 0.5 THz is desirable. Preferably, this range may be further narrowed to 0.3 to 0.4 THz in order to scan for TNT, RDX and many other popular explosives. This may be achieved by making the metal grating with variable grating lines that range from 0.1 mm to 0.075 mm. Alternatively, several gratings, each with their spacing ranging from 0.1 mm to 0.075 mm, may be laid on the chip so that when a ribbon shaped electron beam passes over them, a spectrum of frequencies ranging from 0.3 to 0.4 THz is produced.

Figure 2:
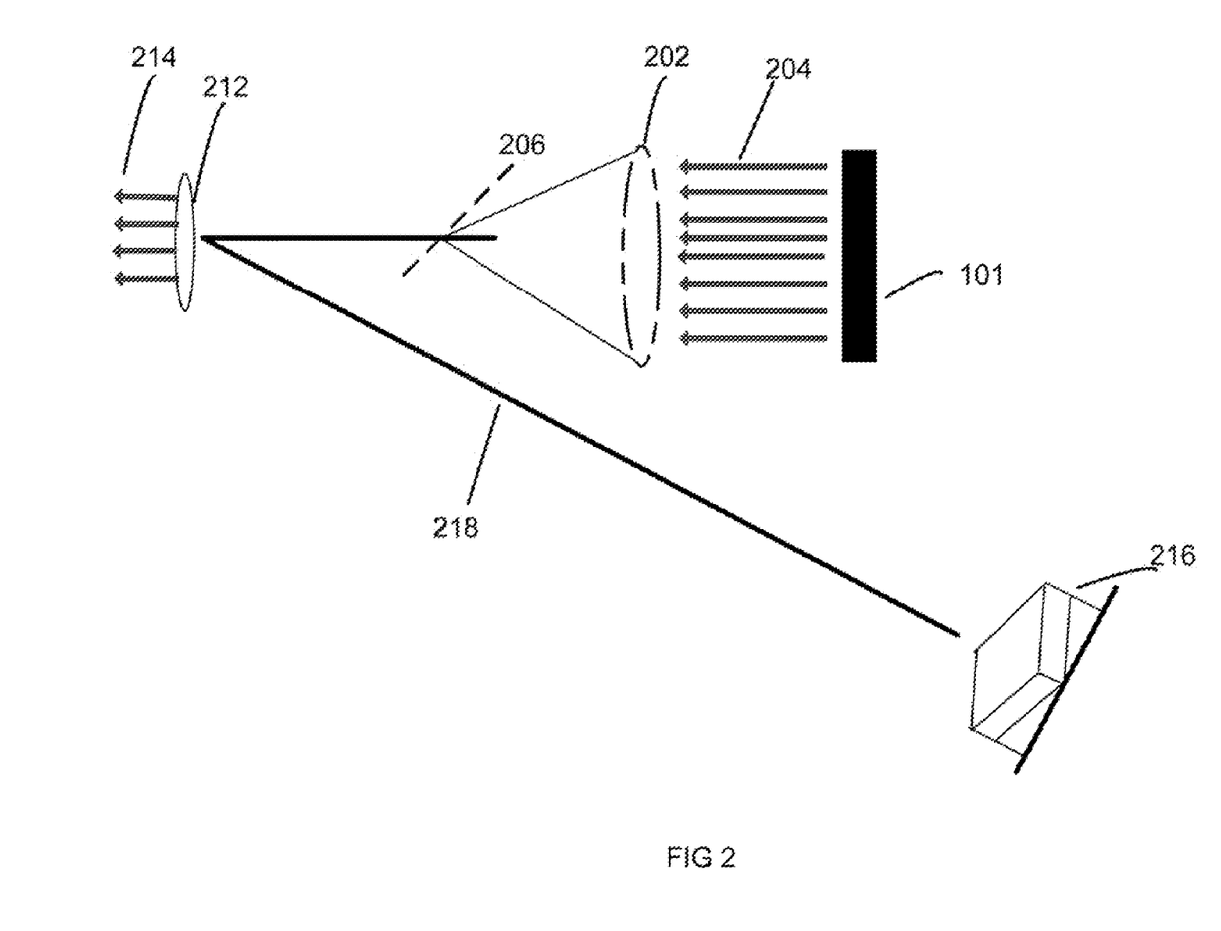
FIG. 2 shows a first preferred embodiment of the present invention.

With reference to FIG. 2, a preferred embodiment of the present invention will now be discussed. As shown in FIG. 2, an exemplary arrangement of portal lenses comprising a Koop's miniaturized THz chip.101, an input coupler 202, a silicon lens wave guide 212 and a for the purposes of this example, a CMOS chip pixel camera 216, is provided. In accordance with a preferred embodiment of the present invention, a human subject may be viewed from front, back, top and bottom. Hundreds of apertures may be needed to cover the entire wall, floor and ceiling surface of the portal. As further shown in FIG. 2, a configuration in which a convex silicon lens may be inserted into each aperture may be used. The THz radiation emanating 204 from the Koop's chip 101 is focused through the input coupler 202 to a focal point of the convex lens 206. The Terahertz waveguide's far end 212 may be located at the focal point 206 of the convex lens so the waves 204, 214 emanated from each aperture may be parallel to each other and normal to the surface of the portal wall. The image reflected from the lens will be sent to an image capturing device 216. Each lens may be designed to view a circle of 1" diameter on the human subject.

The Terahertz waves reflected from the target can be collected on a CMOS or a CCD chip for imaging. In accordance with a preferred embodiment of the present invention, a number of such sources and imaging pixel cameras can be arranged on a grid consisting of horizontal rows and vertical columns along the interior walls of a portal booth for imaging the front and the back of the target. The image of the target is made one pixel at a time using the reflected waves and can be integrated to produce a composite picture using a computer. The irradiation can be simultaneous or sequential in order to minimize the flux incident on the target. The Terahertz reflected off the target is focused on a single pixel Complementary Metal Oxide Semiconductor (CMOS) or Charge Couple Device (CCD) camera. Both of these techniques are mature. The CMOS technique is preferred since it is less expensive.

With regard to the imaging devices, the charge-to-voltage conversion, signal conditioning, noise correction, digitization circuit including amplification can all be incorporated on the same device. CMOS sensors have an advantage over CCD in requiring lower power and producing lower resolution images. The latter attribute can be a consideration for privacy related issues associated with viewing a human body. CMOS is highly efficient in converting the low level electrical energy into photons. Unlike CCD, the CMOS output is digital which can be directly manipulated by the computers.

Although the principle may be the same as a film camera, the inner workings of a digital camera are quite different, the imaging being performed either by a CCD or CMOS sensors. Each sensor element converts light into a voltage proportional to the brightness which is passed into an analogue-to-digital converter (ADC) which translates the fluctuations of the CCD into discrete binary code. The digital output of the ADC is sent to a digital signal processor (DSP), which adjusts contrast and detail, and compresses the image before sending it to the storage medium. The brighter the light, the higher the voltage and the brighter the resulting computer pixel. The more elements, the higher the resolution, and the greater the detail that can be captured.

Rice University found that Terahertz can easily travel on the surface of thin (0.9 mm) stainless steel wires and can be bent to reach places that are not in direct line-of-sight with the source. Accordingly, in order to irradiate the subject normally and to receive reflections from various parts of the human subject in near normal direction, a line of sight is not required. The irradiating Terahertz wave can travel on a straight wire from the source to the lens while the reflected wave can travel on a bent wire. Crosstalk between the direct and reflected waves is avoided by employing a coaxial metallic covering for each wire.

Figure 3:
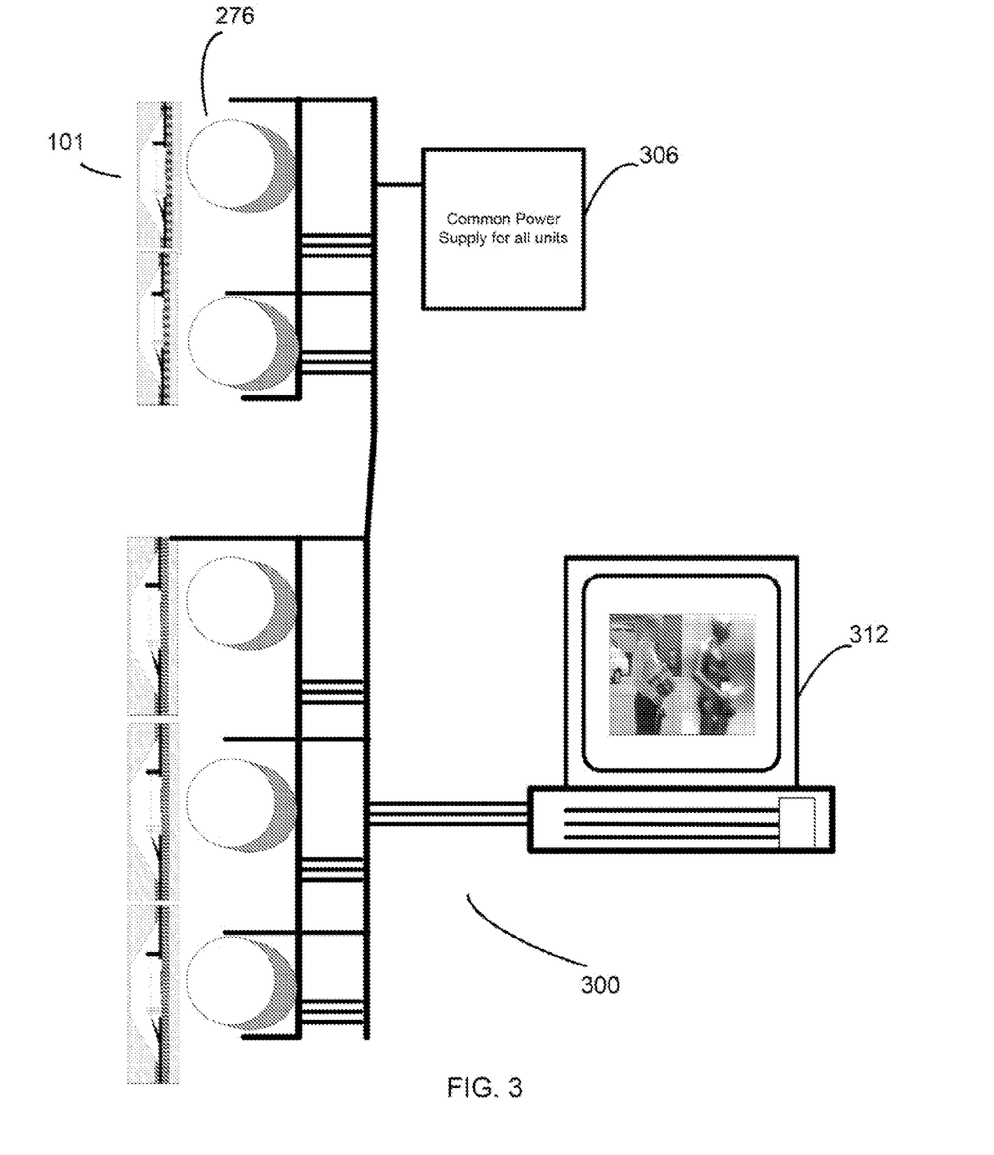
FIG. 3 shows a second preferred embodiment of the present invention.

With reference now to FIG. 3, a functional configuration of a preferred embodiment of the present invention is provided. As shown in FIG. 3, a plurality of low-powered miniaturized Terahertz emitter and detector imaging units 300, each containing a source and/or emitter 101, may be connected by a common power source 306 and a computer 312 which may assemble a spectral image from each detector 276 to identify explosives through a Terahertz signature.

According to a preferred embodiment of the present invention, a plurality of elements comprising emitters 101 and detectors 276 may be arranged in a rectangular grid. Preferably, the vertical columns of the grid may be parallel to the height of the subject and the horizontal rows of elements may correspond to the width of the subject. Such an arrangement may be located on the opposite walls of a booth or chamber for obtaining the explosive spectrum from both sides of the human body.

In an alternative embodiment of the present invention, the coverage in the vertical direction may be obtained by locating the elements comprising emitters 101 and detectors 276 on a single vertical line while the horizontal coverage may be obtained by employing a combination of alternating current and magnets. The beams from each detector may be steered from one side to the other, sweeping an arc of a circle in the horizontal plane. The scan of the whole human body thus may be obtained by such an arrangement and the image of an explosive may be captured if present.

In accordance with a preferred embodiment of the present invention, a portal may constitute two side walls, two open walls, floor and ceiling of a chamber for investigating a subject. The door openings facing each other are for easy entry and easy exit of the subject under investigation. The two open walls may have circular apertures arranged in a two dimensional grid consisting of several rows and columns. The dimensions of the portal and the contours of the walls may be so arranged that an average adult can stand comfortably with no body part more than 10"-12" from the open walls. Viewing from two sides within a portal as described above may allow good coverage for detecting a concealed package strapped on a human body.

In accordance with a preferred embodiment of the present invention, the portal may be enclosed in a bomb proof room to reduce the effect of blast and shrapnel resulting from explosive detonation by a potential suicide bomber. Each pixel camera may capture the image of roughly 0.75 sq in. of the human body. A software integration of the image preferably may be provided by the computer. The computer may also initiate the powering of each source in a simultaneous or sequential manner, from left to right and then from top to bottom. Each Terahertz source may be powered only for the short time that is needed to produce a high contrast image from each camera. Camera outputs may be calibrated periodically or just before each imaging session. Alternatively, since the 1" diameter aperture may leave some voids in the coverage of subject body, a mechanism to rotate the platform by a small angle may be provided. In accordance with another preferred embodiment, the platform can be kept stationary and the walls can be moved by a small angle. Alternatively, a single vertical column of apertures preferably may be used to image the whole human being if the platform is rotated by a full circle. The full rotation of the platform may add to the actual time that the subject is inside a portal undergoing examination.

Figure 4:
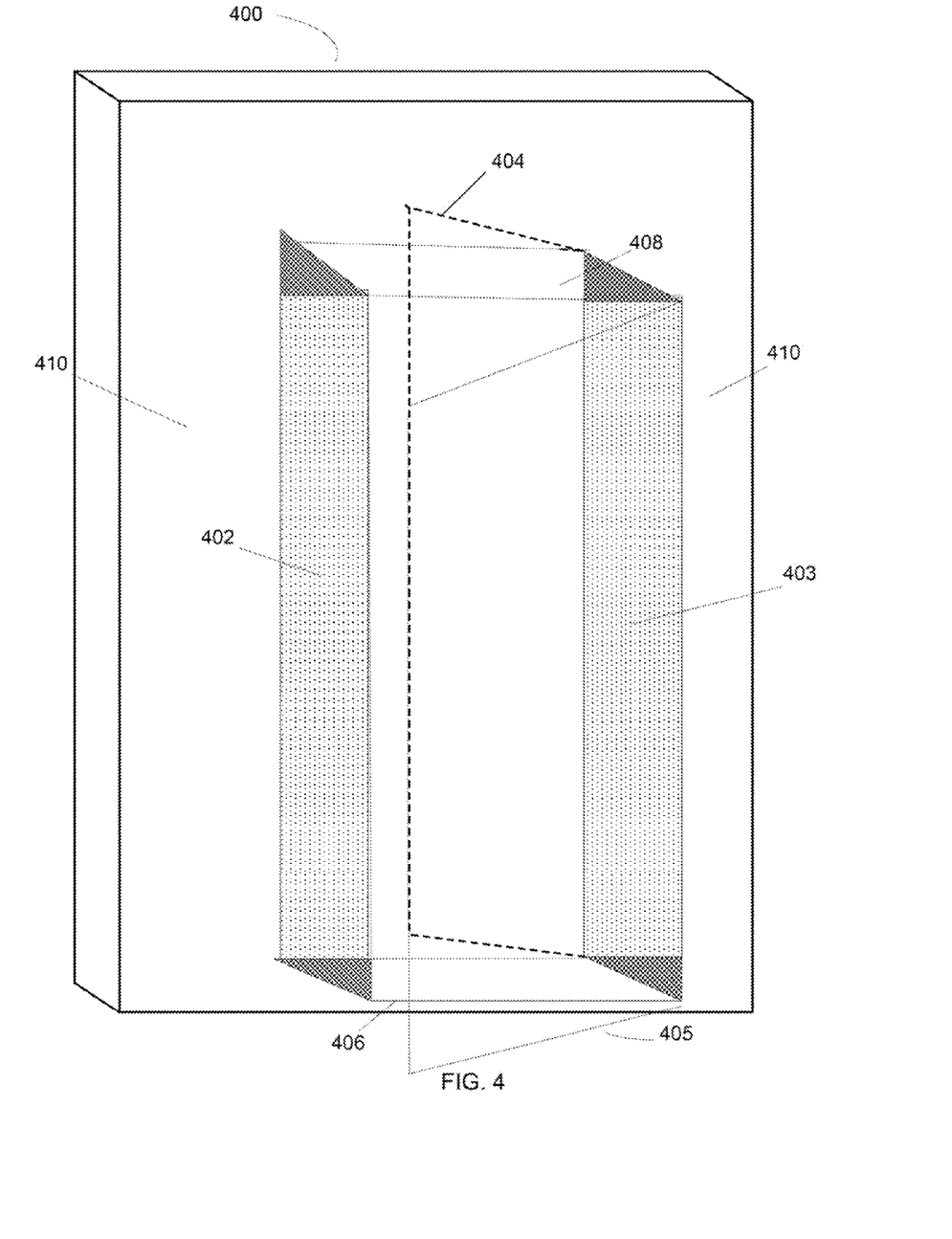
FIG. 4 shows a third preferred embodiment of the present invention.

With reference now to FIG. 4, a further aspect of the preferred embodiment of the present invention will now be discussed. As shown, a portal booth 400 comprising two sidewalls 402/402, a entrance door 404, an exit door 405, a floor 406 and a ceiling 408 of a chamber for investigating a subject, is provided. The entrance door 404 and exit door 405 may be facing each other and may allow for easy entry and easy exit of the subject under investigation. The two sidewalls 602/603 may have circular apertures arranged in a two dimensional grid consisting of several row and columns. In order to cover the entire human body on two sides, from the bottom of the subject's feet to the top of the subject's head, a multitude of apertures may be provided. The inner chamber of the portal booth may be enclosed in a bomb proof room or outer chamber 410 to reduce the effect of any possible blast or shrapnel resulting from a potential explosive detonation.

Figure 5:
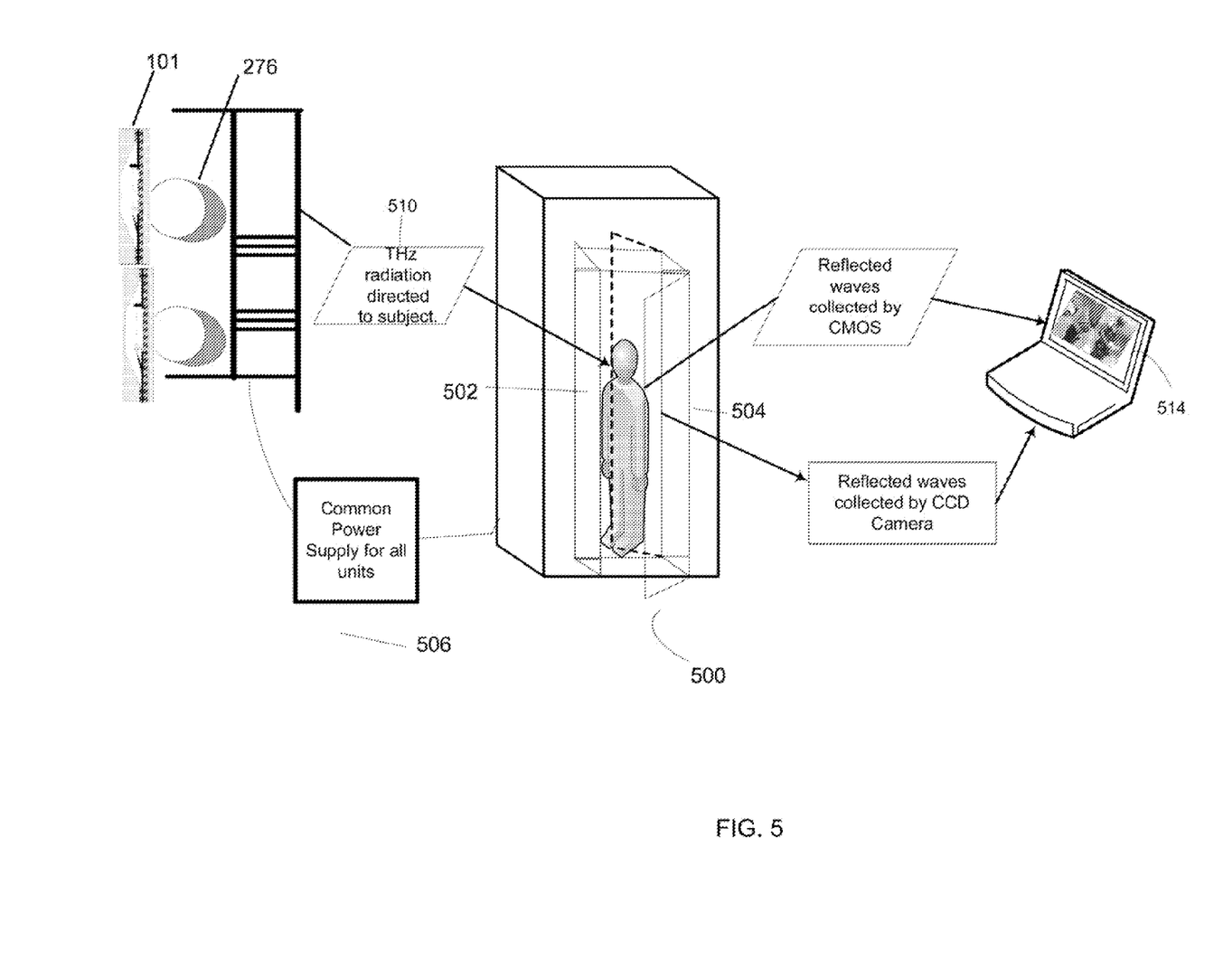
FIG. 5 shows a system diagram of an embodiment of the invention.

With reference now to FIG. 5, a further aspect of the preferred embodiment of the present invention will now be discussed. As shown in FIG. 5, an exemplary system comprising a miniature Terahertz emitter 101 and CMOS or CCD detector imaging units 276 is provided. Preferably, the emitter/detector 101/276 units may be arranged in a rectangular grid contained in both the opposite walls 502/504 of the portal booth 500 in a manner in which all body parts of the subject may be within 10-12" from either wall. Further, a power source 506 may be provided and configured to send voltage to each emitter 101. According to one embodiment of the present invention, the voltage may be adjusted 1 mV to 10 mV and then decreased from 10 mV to 1 mV in a continuous manner at a predetermined rate and pattern. The low power miniature Terahertz emitter 101 may emit THz radiation directed to the subject 510. The THz radiation may be diffused by the subject's clothing, skin, and personal effects and preferably may be detected by a CMOS or CCD pixel camera 276. Preferably the detectors 276 may be monitored by a computer 514 programmed to manipulate an image detected by CMOS or CCD camera using alternative functions which may result in the positive identification of explosives and/or explosive materials. Preferably, computer data may be monitored on-site or remotely in real-time to ensure rapid response time.

In an alternate embodiment of the present invention, emitter/detector units may be arranged in a single vertical line parallel to the subject's height. In this embodiment, the horizontal width of the subject may be irradiated by THz radiation steered by alternating current and magnets which may create a beam. This beam may be steered in a circular arc in the horizontal plane. This arrangement of a single vertical column of emitter/detector units may be confined to one wall 502 in the portal booth 500 or positioned in each opposing wall 502/504 in the portal booth 500.

In a further alternate embodiment, the present invention may be employed where the portal booth 500 is also equipped with a rotating platform to further ensure complete coverage of the subject in the portal booth 500.

While the examples discussed above highlight the use of low-power miniaturized Terahertz emitters in security check point portals, the system may be equally well incorporated at revolving entrance doors, moving walkways, escalators, jet ways and airport doors. Alternatively, implementation of low-power miniaturized Terahertz source and CMOS and/or CCD detector system in auxiliary viewing points may do away with the highly inconvenient security portals altogether. One set or several emitter/detector units may be incorporated into each of the inspection sites. The beam emanating Koop's chip may be steered from one part of the body to the other using magnets.

As detailed herein, the present invention provides a reliable means of generating Terahertz waves and imaging reflected Terahertz waves to detect and confirm the presence of explosives. While the above description contains much specificity, these should not be construed as limitations on the scope, but rather as examples. Many other variations are possible. Accordingly, the scope should be determined not by the embodiments illustrated, but by the appended claims and their legal equivalents.

I claim:

1. An apparatus for detecting the presence of explosives on a target, the apparatus comprising:
    an emitting element, wherein the emitting element is an encapsulated miniaturized Terahertz radiation source configured to direct terahertz radiation against a target;
    a first anode;
    a controllable voltage source connected to the first anode;
    a focusing element;
    a refraction deflecting element;
    a waveguide element;
    a second electrode;
    a detector element comprised of a miniaturized charge coupled device, an aperture, a waveguide wire, and at least one imaging unit for receiving terahertz radiation reflected from the target; and
    a computing element configured to analyze the radiation received by the detector element to identify explosives.

2. The apparatus of claim 1, wherein the detector element comprises a CMOS chip, an aperture, and a wavequide wire.

3. The apparatus of claim 2, wherein the waveguide wire is covered and protected by a coaxial metallic shield.

4. The apparatus of claim 3, wherein the computing element is configured to combine and analyze data collected from a plurality of detectors.

5. A. method for detecting the presence of explosives on a target, the method comprising the steps of:
    providing an emittinq element, wherein the emitting element is an encapsulated miniaturized Terahertz radiation source configured to direct terahertz radiation against a target;
    emitting an electron beam from a first anode connected to a controllable voltage source;
    focusing the electron beam through a focusing element;
    deflecting the focused electron beam across a refraction deflecting element;
    directing the THz radiation across a waveguide element;
    applying voltage to a second electrode to further stabilize and direct the THz radiation;
    providing a plurality of detector elements wherein each detector element comprises a miniaturized charged coupled device, an aperture, a waveguide wire, and at least one imaging unit for receiving terahertz radiation reflected from the target; and
    analyzing radiation received from at least one detector element to identify explosives.

* * * * *